United States Patent
Boyd, Sr.

(10) Patent No.: US 6,666,212 B2
(45) Date of Patent: Dec. 23, 2003

(54) INTRAORAL DISCLUDER DEVICE AND METHOD FOR PREVENTING MIGRAINE AND TENSION HEADACHES AND TEMPOROMANDIBULAR DISORDERS

(76) Inventor: James P. Boyd, Sr., 710 Midori Ct., Solana Beach, CA (US) 92075

(*) Notice: Subject to any disclaimer, the term of this patent is extended or adjusted under 35 U.S.C. 154(b) by 0 days.

(21) Appl. No.: 10/033,693

(22) Filed: Dec. 27, 2001

(65) Prior Publication Data

US 2003/0121523 A1 Jul. 3, 2003

(51) Int. Cl.[7] .............................................. A61C 5/14
(52) U.S. Cl. ........................ 128/859; 128/861; 433/41
(58) Field of Search ................................ 128/846, 848, 128/859–862; 433/6, 41; 602/902

(56) References Cited

U.S. PATENT DOCUMENTS

| | | | |
|---|---|---|---|
| 2,694,397 A | 11/1954 | Herms | 128/136 |
| 2,808,898 A | 10/1957 | Meyerhoefer | 183/51 |
| 3,478,429 A | 11/1969 | Shilliday | 32/14 |
| 3,513,838 A | 5/1970 | Foderick et al. | 128/136 |
| 3,705,585 A * | 12/1972 | Saffro | 128/303.1 |
| 4,211,008 A | 7/1980 | Lerman | 433/229 |
| 4,413,979 A * | 11/1983 | Ginsburg | 433/41 |
| 4,468,196 A | 8/1984 | Keller | 433/24 |
| 4,559,013 A | 12/1985 | Amstutz et al. | 433/22 |
| 4,624,640 A | 11/1986 | Tesini | 433/71 |
| 4,773,853 A | 9/1988 | Kussick | 433/6 |
| 4,798,534 A | 1/1989 | Breads | 433/6 |
| 4,892,478 A | 1/1990 | Tateosian et al. | 433/6 |
| 4,915,630 A | 4/1990 | Honig | 433/215 |
| 4,920,984 A | 5/1990 | Furumichi et al. | 128/861 |
| 4,997,182 A | 3/1991 | Kussick | 272/95 |
| 5,031,611 A | 7/1991 | Moles | 128/201 |
| 5,033,480 A | 7/1991 | Wiley et al. | 128/861 |
| 5,067,896 A | 11/1991 | Korn | 433/6 |
| 5,085,584 A | 2/1992 | Boyd | 433/6 |
| 5,092,346 A | 3/1992 | Hays et al. | 128/848 |
| 5,277,203 A | 1/1994 | Hays | 128/861 |
| 5,503,552 A | 4/1996 | Diesso | 433/37 |
| 5,513,656 A | 5/1996 | Boyd, Sr. | 128/859 |
| 5,554,665 A | 9/1996 | Tateosian et al. | 522/30 |
| 5,624,257 A | 4/1997 | Farrell | 433/6 |
| 5,779,470 A | 7/1998 | Kussick | 433/6 |
| 5,795,150 A | 8/1998 | Boyd | 433/6 |
| 5,885,073 A | 3/1999 | Kussick | 433/6 |
| 6,231,337 B1 | 5/2001 | Boyd | 433/6 |

* cited by examiner

*Primary Examiner*—Michael A. Brown
(74) *Attorney, Agent, or Firm*—Sheppard, Mullin Richter & Hampton LLP

(57) ABSTRACT

A semi-custom intraoral discluder device for preventing chronic tension and common migraine headaches and temporomandibular disorders that are caused or perpetuated by chronic activity of the temporalis muscle. The discluder includes a trough, contoured to encompass at least one maxillary or mandibular incisor, from which extends a protrusion, typically of a dome shape. The trough can be retained on the teeth by any adaptable material which can flow around the teeth and then maintain its shape. The adaptation of the retentive material can be performed by the end user, health care provider, or anyone trained in the art. Once in place in the wearer's mouth, one or two opposing incisor teeth will come into contact with the protrusion prior to the upper and lower posterior and/or canine teeth coming into contact, regardless of the position of the mandible, thereby reducing the intensity of the activity of the temporalis muscle.

20 Claims, 2 Drawing Sheets

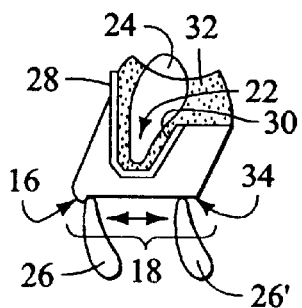
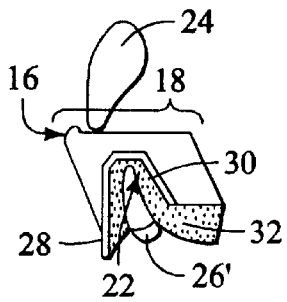
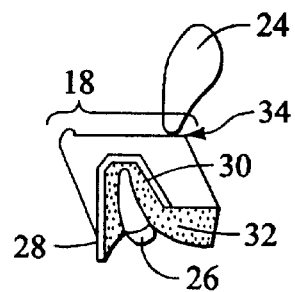
FIGURE 5  FIGURE 6  FIGURE 7
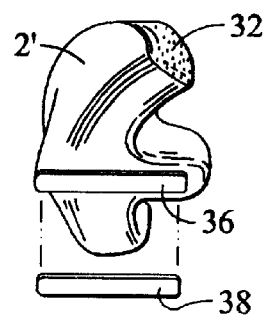
FIGURE 8
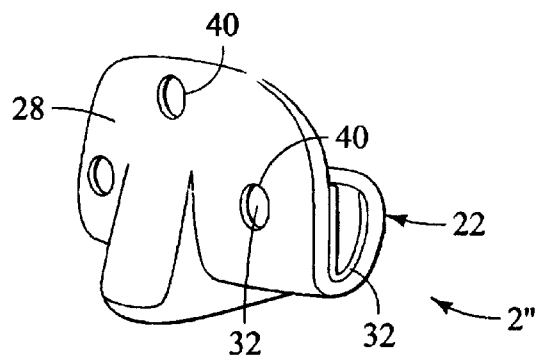
FIGURE 9

INTRAORAL DISCLUDER DEVICE AND METHOD FOR PREVENTING MIGRAINE AND TENSION HEADACHES AND TEMPOROMANDIBULAR DISORDERS

BACKGROUND OF THE INVENTION

The present invention relates generally to intraoral devices and, more particularly, to an intraoral discluder device for use in relieving tension headaches, common migraine headaches, and temporomandibular disorders.

Tension and muscle contraction headaches affect many people every day. The headaches are often recurring and, without effective treatment, can become very painful, restricting an individual's ability to think clearly and function effectively. The discomfort associated with tension and muscle contraction headaches is usually due to pain from strained and fatigued muscles of the head. The majority of the muscles of the human head are not sufficiently strong to elicit the type of pain and discomfort associated with tension and muscle contraction headaches. That is not the case with the temporalis muscle, however, which is located on the side of the skull and extends from just behind the eye to just behind the ear, and which is an extremely powerful muscle that functions to close or elevate the jaw.

Under normal circumstances, the temporalis muscle should not exert a large static force by contracting isometrically, except possibly during normal chewing. Inappropriate isometric contraction of temporalis muscle is commonly known as "clenching" and clinically known as myofascial dysfunction. Unfortunately, myofacial dysfunction is particularly difficult to detect or diagnose because the act of clenching is a relatively motionless act that is commonly done while a person is concentrating on another topic, or while sleeping.

As the muscular contraction condition of "clenching" continues, the muscle becomes fatigued and susceptible to spasm and cramping. The pain from spasming and cramping temporalis fibers is severe and is usually diagnosed as a common migraine. Individuals suffering from headaches, who seek the assistance of a physician, are usually treated with muscle relaxants, analgesics, and physical therapy for the muscle fatigue. However, medications and therapy require continual treatment and treat only the symptoms of the underlying problem and not the problem itself.

Persons suffering from headaches, who seek the assistance of a dentist, commonly will be diagnosed with a temporomandibular disorder and treated with an intraoral "jaw positioning" appliance. Unfortunately, the intraoral appliances provided by dentists usually are not entirely effective, because they only approximate the relative positions of the upper and lower teeth with respect to each other, allowing clenching to continue with minimal mandibular movement. Further, these intraoral appliances ordinarily cannot be used with patients who have malocclusions, protrusions or retrusions of the mandible, or other irregular teeth or mandibular orientations. Typically, the intraoral appliance must also be fabricated by a dentist at a prohibitive cost to a majority of individuals who suffer from tension and common migraine headaches. Lastly, most intraoral jaw positioning appliances and other types of semi-custom intraoral discluders can only be used on the upper teeth. However, in some circumstances, use of the device on the upper teeth is impossible due to malocclusions and irregular orientation of the teeth.

It should be apparent from the foregoing discussion, that there is need for a more effective semi-custom intraoral device that can be used with various teeth and jaw orientations and that can be placed on either the upper teeth or the lower teeth to prevent contact of the upper and lower teeth in all mandibular movements. By preventing contact of the upper and lower teeth, the semi-custom intraoral discluder would be able to inhibit inappropriate isometric contraction of the temporalis muscle and thereby prevent tension and common migraine headaches and other temporomandibular disorders. The present invention satisfies this need.

SUMMARY OF THE INVENTION

The above-noted problems, and others, are overcome in accordance with this invention by a small semi-custom intraoral discluder device that can be used with various teeth and jaw orientations and that can be placed on either the upper teeth or the lower teeth, to prevent contact of opposing upper and lower teeth. By preventing contact of the upper and lower teeth, the semi-custom intraoral discluder device inhibits inappropriate isometric contraction of the temporalis muscle, thereby preventing tension and common migraine headaches and other temporomandibular disorders.

The intraoral discluder device of the invention includes a prefabricated trough, having a front wall and a rear wall. Extending a substantially distance anteriorly and posteriorly from the trough is a protrusion, typically dome shaped, that extends such that as the lower jaw is elevated, the edge of the opposing incisor or incisors comes into contact with the contact surface of the protrusion prior to the opposing upper and lower teeth coming into contact. The contact surface of the protrusion prevents the upper and lower teeth from contacting each other, regardless of the protrusive, retrusive, or excursive position of the mandible or the teeth or any mandibular movement and suppresses isometric contraction of the temporalis muscle. The protrusion can be further modified by the practitioner or wearer to accommodate for any unusual or extreme mandibular movements or teeth orientations.

If necessary, the trough can be filled with an adaptable material that conforms to the shape of the incisors and assists in retaining the trough on the upper or lower incisors. In addition, means can be provided for enhancing retention of the adaptable material within the trough. Such retaining means can take the form of one or more cutouts formed in a wall of the trough, a mechanical undercut in a wall of the trough, an adhesive, and/or natural attraction of the adaptable material to the trough.

In other, more detailed features of the invention, the protrusion preferably has a length in the anterior/posterior direction in the range of about 8 mm to about 12 mm. Further, the protrusion preferably projects anteriorly from the front wall by at least about 3 mm.

Other features, and advantages of the present invention should become apparent from the following description of the preferred embodiments, taken in conjunction with the accompanying drawings, which illustrate, by way of example, the principles of the invention.

BRIEF DESCRIPTION OF THE DRAWINGS

Embodiments of the present invention will now be described, by way of example only, with reference to the following drawings in which:

FIG. 5 is a side sectional view of the intraoral discluder of FIG. 2, in place over a maxillary incisor with an adaptable material conforming to the shape of the maxillary incisor, opposing a mandibular incisor, with the mandibular incisor shown in both a protrusive and a retrusive position.

FIG. 6 is a side sectional view of the intraoral discluder of FIG. 2, in place over a mandibular incisor with an adaptable material conforming to the shape of the mandibular incisor, opposing a maxillary incisor, with the mandible in a retruded position.

FIG. 7 is a side sectional view of the intraoral discluder of FIG. 2, similar to the view of FIG. 6, but with the mandible in a protruded position.

FIG. 8 is a perspective view of an alternative embodiment of a semicustom intraoral discluder in accordance with the invention, including a trough filled with an adaptive material, a protrusion, and one extending tab placed on the protrusion and another extending tab aligned for placement on the first extending tab.

FIG. 9 is a perspective view of another alternative embodiment of a semi-custom intraoral discluder in accordance with the invention, this embodiment differing from the discluder embodiment of FIG. 2 in that the front wall of its trough includes cutouts for enhancing retention of the adaptable material.

DETAILED DESCRIPTION OF THE PREFERRED EMBODIMENTS

Figure 1:
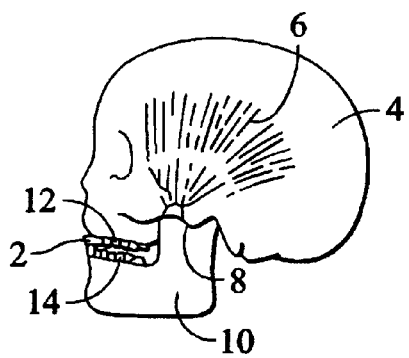
FIG. 1 is a schematic side elevation view of the human skull with a preferred embodiment of a semi-custom intraoral discluder of the invention positioned over the maxillary teeth.
Figure 2:
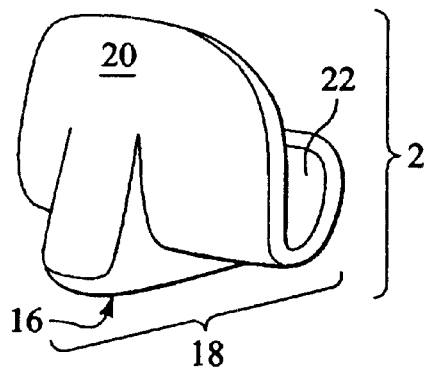
FIG. 2 is a perspective view of the intraoral discluder of FIG. 1.

With reference now to the exemplary drawings, and particularly to FIGS. 1 and 2, there is shown a semi-custom intraoral discluder 2 in accordance with the invention, which functions to prevent tension and common migraine headaches and temporomandibular disorders. With particular reference to FIG. 1, a schematic representation of a human skull 4 is shown, wherein the temporalis muscle 6 extends from the skull to its attachment 8 on the mandible 10. A contraction of the temporalis muscle causes the jaw to close. The discluder prevents the upper teeth 12 and the lower teeth 14 from contacting each other and thereby inhibits inappropriate contraction of the temporalis muscle.

The discluder 2 includes a trough 22 with a labial wall 20 and a protrusion 18 with an anterior contact surface 16 extending from the labial wall of the trough. The discluder may be made of any biocompatible material that will hold its form, including, e.g., polymers, enamels, rubbers, silicone resins, and any other materials that would be known to be used by those skilled in the art. In an alternative embodiment, the protrusion and the trough may be made of different biocompatible materials selected from these same examples.

Figure 3:
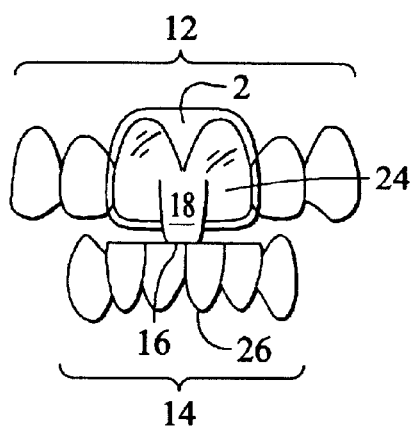
FIG. 3 is a front elevational view of the intraoral discluder of FIG. 2, in place over the maxillary teeth, opposing the mandibular incisors.

FIG. 3 shows the intraoral discluder 2 in place over the maxillary incisors 24, with the contact surface 16 of the protrusion 18 contacting the opposing mandibular incisors 26 when the mandible 10 elevates. The contact surface is positioned a sufficient distance away from the trough 22 to prevent the opposing upper teeth 12 and lower teeth 14 from contacting each other. Typically, this distance is on the order of several millimeters.

With reference now to FIG. 5, the trough 22 of the intraoral discluder 2 is defined by a front wall 28 and a rear wall 30. An adaptive material 32 can optionally be disposed within the trough, for conforming engagement with the maxillary incisors 24. This adaptive material may be made of any type of material that conforms and retains its shape, including, e.g., silicone resins, polymers, enamels, rubbers, and any other material that would be known to be used by those skilled in the art. This material aids in providing a comfortable and durable engagement between the discluder and the incisors.

In one feature of the invention, the protrusion 18 projects both anteriorly and posteriorly from the trough 22. This ensures that the opposing mandibular incisors 26 will contact the contact surface 16 of the protrusion 18 regardless of whether the mandible is in a protrusive position or a retrusive position. These two positions are depicted in FIG. 5, with the mandibular incisor being identified by the reference numeral 26 when it is in a protrusive position and by the reference numeral 26' when it is in a retrusive position. Preferably, the protrusion has a length in the anterior/posterior direction in the range of about 8 mm to about 12 mm. It projects anteriorly from the front wall 28 of the trough by at least about 3 mm.

Figure 4:
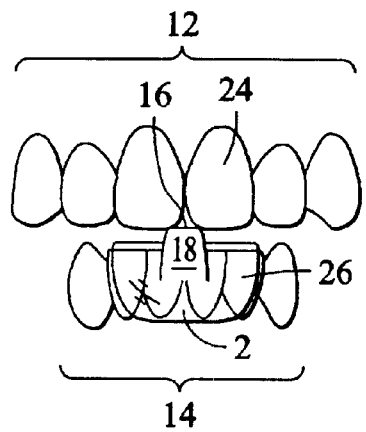
FIG. 4 is a front elevational view of the intraoral discluder of FIG. 2, in place over the mandibular teeth, opposing the maxillary incisors.

Alternatively, as shown in FIG. 4, the intraoral discluder 2 can be placed over the mandibular incisors 26, with the contact surface 16 of the protrusion 18 contacting the opposing maxillary incisors 24 when the mandible 10 elevates. As in the case when the discluder is placed over the maxillary incisors, this prevents the opposing upper and lower teeth 12, 14 from contacting each other.

FIGS. 6 and 7 show the discluder 2 positioned on the mandibular incisors, with its trough 22 being held in place by the adaptive material 32 around the mandibular incisor 26. In FIG. 6, the opposing maxillary incisor 24 contacts an anterior portion of the contact surface 16 of the protrusion 18 when the mandible is in a retrusive position. In FIG. 7, on the other hand, the opposing maxillary incisor contacts a posterior portion of the contact surface when the mandible is in a protrusive position.

An alternative embodiment of a semi-custom intraoral discluder 2' in accordance with the invention is depicted in FIG. 8. It includes a trough 22 and a protrusion 18 projecting both anteriorly and posteriorly from the trough. An adaptive material 32 is disposed within the trough, and two extending tabs 36, 38 are included for placement on the protrusion, to increase the distance of the contacting surface 16 from the trough. The extending tab 36 is shown secured to the protrusion, and the extending tab 38 is shown in alignment with the tab 36. These tabs are selectively used if the wearer's mouth is configured such that the upper teeth 12 and the lower teeth 14 contact each other before the opposing incisors 24 or 26 contact the protrusion. The wearer or practitioner can selectively adhere one or more of these extension tabs to the occluding face of the protrusion to increase the distance between the contact surface and the trough. The extension tabs may be made of any suitable biocompatible material, including, e.g., silicone resins, polymers, enamels, rubbers, and any other material known to those skilled in the art. The extension tabs may be adhered to the entire protrusion, as shown, or to only a portion of the protrusion. The extension tabs may be adhered by any suitable method, including, e.g., adhesives, cutouts, prefabricated snap-in-place pieces, natural attraction, adhesion, or other any other suitable method known to those skilled in the art.

Another alternative embodiment of a semi-custom intraoral discluder 2" in accordance with the invention is depicted in FIG. 9. This discluder includes a trough 22 and a protrusion 18 projecting both anteriorly and posteriorly from the trough, and an adaptive material 32 is disposed within the trough. This discluder further includes three circular cutouts 40 in the trough's front wall 28, for enhancing the retention of the adaptive material within the trough. Other structures for enhancing retention of the adaptive material could include mechanical undercuts, adhesives, and/or natural attraction of the adaptable material to the trough.

It should be evident from the drawings and the discussion above that the semi-custom intraoral discluder 2 of the invention may be used on either the upper teeth 12 or lower teeth 14 and with various teeth and jaw orientations, to prevent the upper teeth and lower teeth from contacting each other and causing inappropriate isometric contractions of the temporalis muscle 6. The intraoral semi-custom discluder of the invention prevents tension and common migraine headaches and temporomandibular disorders that result from inappropriate isometric contraction of the temporalis muscle.

Although the invention has been described in detail with reference to the presently preferred embodiments, those of ordinary skill in the art will appreciate that various modifications can be made without departing from the invention. Accordingly, the invention is defined only by the following claims.

I claim:

1. A semi-custom intraoral discluder device comprising:
   a prefabricated trough defining a first axis and having a front wall and a rear wall sized and configured to accommodate at least one upper or lower incisor, wherein the front wall is disposed is adjacent to the front of the incisor when the trough is in the wearer's mouth; and
   a protrusion attached to the trough and projecting anteriorly from the front wall of the trough and posteriorly from the rear wall of the trough when the trough is in the wearer's mouth, wherein the protrusion defines a second axis generally perpendicular to the first axis of the trough, and wherein the protrusion is sized and configured to prevent contact between opposing upper and lower teeth, including when the mandible is in a protrusive position or a retrusive position.

2. The intraoral discluder device according to claim 1, and further comprising a quantity of adaptable material disposed within the trough and adapted to conform to the shape of the incisor, to assist in retaining the device in the wearer's mouth.

3. The intraoral discluder device according to claim 2, and further comprising means for retaining the adaptable material within the trough.

4. The intraoral discluder device according to claim 3, wherein the means for retaining includes one or more cutouts formed in a wall of the trough.

5. The intraoral discluder device according to claim 2, wherein the means for retaining is selected from the group consisting of a mechanical undercut in a wall of the trough, an adhesive, and natural attraction of the adaptable material to the trough.

6. The intraoral discluder device according to claim 1, wherein the trough and the protrusion both are fabricated from a biocompatible material.

7. The intraoral discluder device according to claim 1, wherein the protrusion comprises a plurality of tabs that increase the distance from at least one opposing incisor to the trough.

8. The intraoral discluder device according to claim 1, wherein the protrusion is configured not to move when contacted by at least one opposing incisor.

9. The intraoral discluder device according to claim 1, wherein the protrusion has a length in the anterior/posterior direction in the range of about 8 mm to about 12 mm.

10. The intraoral discluder device according to claim 9, wherein the protrusion projects anteriorly from the front wall by at least about 3 mm.

11. A method for using a semi-custom intraoral discluder device, comprising the steps of:
    providing a semi-custom intraoral discluder device that includes
       a trough defining a first axis and having a front wall and a rear wall sized and configured to accommodate at least one upper or lower incisor, wherein the front wall is disposed adjacent to the front of the incisor and the rear wall is disposed adjacent to the rear of the incisor when the trough is in the wearer's mouth, and
       a protrusion attached to the trough and projecting anteriorly from the front wall of the trough and a posteriorly from the rear wall of the trough when the tough is in the wearer's mouth, wherein the protrusion defines a second axis generally perpendicular to the first axis of the trough, and wherein the protrusion is sized and configured to prevent contact between opposing upper and lower teeth; and
    placing the intraoral discluder device on at least one of the wearer's upper or lower incisors so that the protrusion will contact at least one opposing incisor tooth prior to contact between upper and lower teeth, including when the mandible is in a protrusive position or a retrusive position.

12. The method according to claim 11, and further including a step of placing a quantity of adaptable material into the trough, such material conforming to the shape of the at least one upper or lower incisor, thereby assisting in retaining the device in the wear's mouth.

13. The method according to claim 12, wherein the semi-custom intraoral discluder device provided in the step of providing further includes means for retaining the adaptable material within the trough.

14. The intraoral discluder device according to claim 13, wherein the means for retaining is selected from the group consisting of one or more cutouts formed in a wall of the trough, a mechanical undercut in a wall of the trough, an adhesive, and natural attraction of the adaptable material to the trough.

15. The method according to claim 11, wherein the trough and protrusion are fabricated from a biocompatible material.

16. The method according to claim 11, and further including a step of securing at least one prefabricated tab to the protrusion, to increase the distance from at least one opposing incisor to the trough.

17. The method according to claim 11, wherein the protrusion is configured not to move when contacted by at least one opposing incisor.

18. The method according to claim 11, wherein the protrusion has a length in the anterior/posterior direction in the range of about 8 mm to about 12 mm.

19. The method according to claim 11, wherein the protrusion projects anteriorly from the front wall by at least about 3 mm.

20. A semi-custom intraoral discluder device comprising:
    a prefabricated trough defining a first axis and having a front wall and a rear wall sized and configured to accommodate at least one upper or lower incisor, wherein the front wall is disposed is adjacent to the front of the incisor when the trough is in the wearer's mouth;

a quantity of adaptable material disposed within the trough and adapted to conform to the shape of the incisor, to assist in retaining the device in the wearer's mouth;

means for retainind the adaptable material within the trough; and a protrusion attached to the trough and projecting anteriorly from the front wall of the trough and posteriorly from the rear wall of the trough when the trough is in the wearer's mouth;

wherein the trough, the adaptable material, and the protrusion all are formed of a biocompatible material;

wherein the protrusion has a length in the anterior/posterior direction in the range of about 8 mm to about 12 mm, and wherein the protrusion projects anteriorly from the front wall of the trough by at least about 3 mm, and wherein the protrusion defines a second axis generally perpendicular to the first axis of the trough, and wherein the protrusion is sized and configured to prevent contact between opposing upper and lower teeth, including when the mandible is in a protrusive position or a retrusive position.

* * * * *

UNITED STATES PATENT AND TRADEMARK OFFICE
CERTIFICATE OF CORRECTION

PATENT NO.     : 6,666,212 B2
DATED          : December 23, 2003
INVENTOR(S)    : James P. Boyd Sr.

It is certified that error appears in the above-identified patent and that said Letters Patent is hereby corrected as shown below:

Column 6,
Line 24, change "tough" to -- trough --
Line 39, change "wear's" to -- wearer's --

Column 7,
Line 9, change "retainind" to -- retaining --

Signed and Sealed this

Twenty-fourth Day of February, 2004

JON W. DUDAS
*Acting Director of the United States Patent and Trademark Office*